United States Patent
Burstein

(10) Patent No.: US 10,806,890 B2
(45) Date of Patent: Oct. 20, 2020

(54) METHOD AND APPARATUS FOR MANAGING PHOTOPHOBIA AND MIGRAINE PHOTOPHOBIA

(71) Applicant: Beth Israel Deaconess Medical Center, Inc., Boston, MA (US)

(72) Inventor: Rami Burstein, Chestnut Hill, MA (US)

(73) Assignee: BETH ISRAEL DEACONESS MEDICAL CENTER, INC., Boston, MA (US)

( * ) Notice: Subject to any disclaimer, the term of this patent is extended or adjusted under 35 U.S.C. 154(b) by 181 days.

(21) Appl. No.: 15/736,555

(22) PCT Filed: Jun. 17, 2016

(86) PCT No.: PCT/US2016/038107
§ 371 (c)(1),
(2) Date: Dec. 14, 2017

(87) PCT Pub. No.: WO2016/205669
PCT Pub. Date: Dec. 22, 2016

(65) Prior Publication Data
US 2018/0177976 A1 Jun. 28, 2018

Related U.S. Application Data

(60) Provisional application No. 62/336,364, filed on May 13, 2016, provisional application No. 62/182,347, filed on Jun. 19, 2015.

(51) Int. Cl.
*A61M 21/02* (2006.01)
*G02C 7/10* (2006.01)
(Continued)

(52) U.S. Cl.
CPC .......... *A61M 21/02* (2013.01); *A61B 3/0008* (2013.01); *F21S 6/003* (2013.01); *F21S 8/04* (2013.01);
(Continued)

(58) Field of Classification Search
CPC .... A61N 2005/0658; A61N 2005/0662; A61N 2005/0663; A61N 5/0613–0625; A61N 2005/0648
See application file for complete search history.

(56) References Cited

U.S. PATENT DOCUMENTS

| 5,447,527 A | 9/1995 | Waldman |
| 5,530,628 A | 6/1996 | Ngai |

(Continued)

FOREIGN PATENT DOCUMENTS

JP 64-063201 A 3/1989

OTHER PUBLICATIONS

"Environment", accessed Mar. 4, 2020, Merriam-Webster.com, https://www.merriam-webster.com/dictionary/environment (Year: 2020).*
PCT/US2016/38107, Aug. 18, 2016, Invitation to Pay Additional Fees.
PCT/US2016/38107, Dec. 7, 2016, International Search Report and Written Opinion.
(Continued)

*Primary Examiner* — Michael W Kahelin
(74) *Attorney, Agent, or Firm* — Daniel C. Pierron; Widerman Malek, PL

(57) ABSTRACT

Apparatus and methods for producing narrow-band radiation in the green region of the visible spectrum are described. The narrow-band radiation may be used to aid subjects experiencing photophobia. In some cases, subjects may experience a reduction in pain (e.g., migraine photophobia) when using the narrow-band radiation.

23 Claims, 9 Drawing Sheets

(51) Int. Cl.

| | | |
|---|---|---|
| *A61B 3/00* | (2006.01) | |
| *F21V 9/30* | (2018.01) | |
| *F21S 6/00* | (2006.01) | |
| *F21S 8/04* | (2006.01) | |
| *F21V 9/08* | (2018.01) | |
| *F21V 23/02* | (2006.01) | |
| *F21V 8/00* | (2006.01) | |
| *F21Y 115/30* | (2016.01) | |
| *F21Y 115/10* | (2016.01) | |
| *A61M 21/00* | (2006.01) | |
| *A61N 5/06* | (2006.01) | |
| *A61N 5/067* | (2006.01) | |
| *F21V 3/04* | (2018.01) | |
| *F21V 5/04* | (2006.01) | |

(52) U.S. Cl.
CPC .................. *F21V 9/08* (2013.01); *F21V 9/30* (2018.02); *F21V 23/02* (2013.01); *G02B 6/0011* (2013.01); *G02C 7/104* (2013.01); *A61M 2021/0044* (2013.01); *A61N 5/0618* (2013.01); *A61N 2005/067* (2013.01); *A61N 2005/0648* (2013.01); *A61N 2005/0652* (2013.01); *A61N 2005/0654* (2013.01); *A61N 2005/0663* (2013.01); *A61N 2005/0667* (2013.01); *F21S 6/005* (2013.01); *F21V 3/049* (2013.01); *F21V 5/04* (2013.01); *F21Y 2115/10* (2016.08); *F21Y 2115/30* (2016.08); *G02C 2202/10* (2013.01)

(56) References Cited

U.S. PATENT DOCUMENTS

| | | | |
|---|---|---|---|
| 5,690,421 | A | 11/1997 | Shea et al. |
| 6,350,275 | B1* | 2/2002 | Vreman ................ A61M 21/00 607/88 |
| 7,883,534 | B1 | 2/2011 | Crosby |
| 2002/0029071 | A1* | 3/2002 | Whitehurst .......... A61N 5/0613 607/88 |
| 2003/0223036 | A1 | 12/2003 | Anderson et al. |
| 2006/0077662 | A1 | 4/2006 | Dean et al. |
| 2006/0125418 | A1 | 6/2006 | Bourgault |
| 2006/0158090 | A1 | 7/2006 | Wang et al. |
| 2006/0262272 | A1* | 11/2006 | Anderson .............. A61B 3/066 351/221 |
| 2009/0222070 | A1* | 9/2009 | Daffer ................. A61N 5/0613 607/91 |
| 2012/0041520 | A1* | 2/2012 | Colbaugh ........... A61N 5/0618 607/88 |
| 2013/0053929 | A1* | 2/2013 | Colbaugh ............ A61M 21/02 607/90 |

OTHER PUBLICATIONS

Invitation to Pay Additional Fees for Application No. PCT/US2016/38107 dated Aug. 18, 2016.

International Search Report and Written Opinion for Application No. PCT/US2016/38107 dated Dec. 7, 2016.

Noseda et al., Migraine photophobia originating in cone-driven retinal pathways. Brain: A Journal of Neurology. 2016;1-16.

* cited by examiner

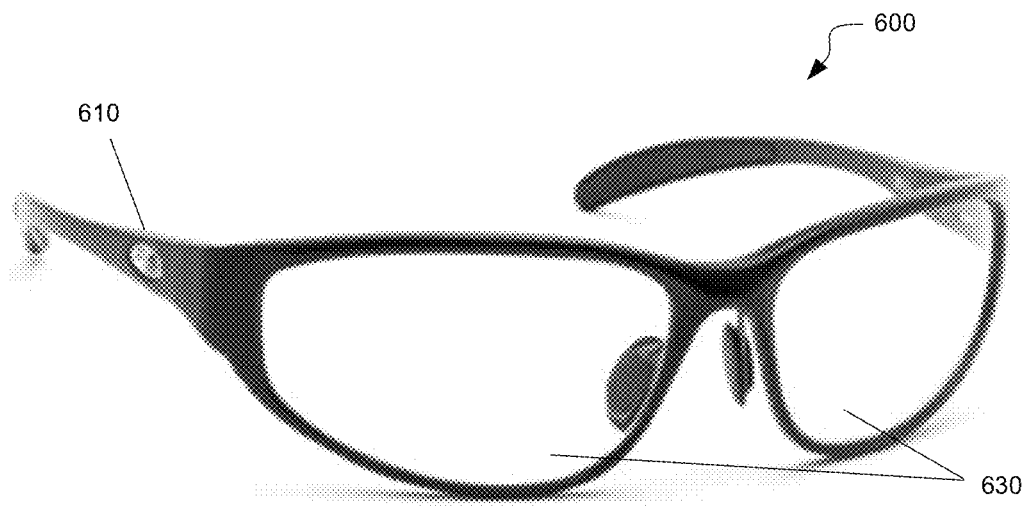
FIG. 6A
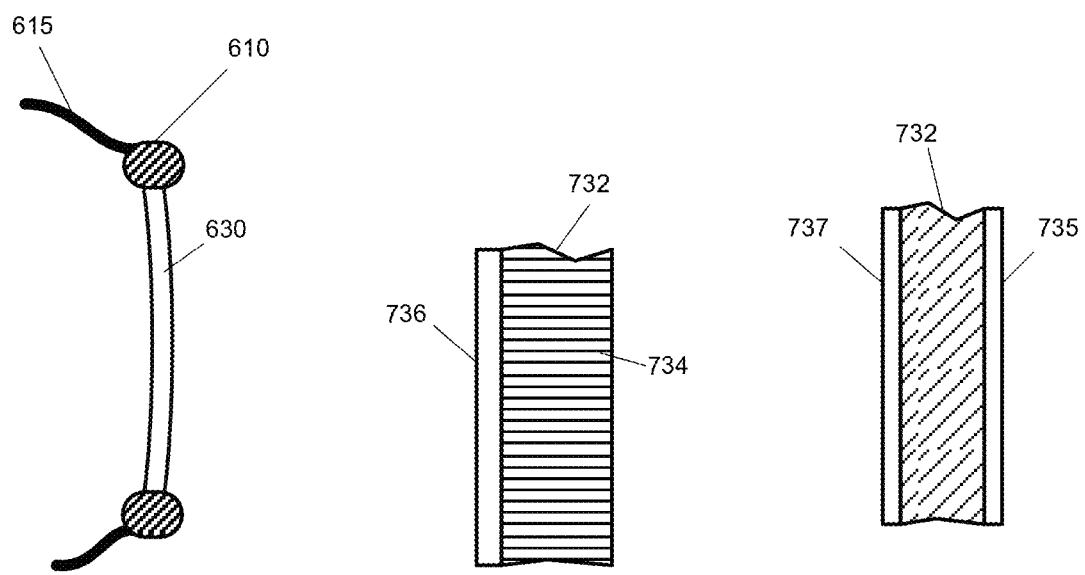
FIG. 6B  FIG. 7A  FIG. 7B

METHOD AND APPARATUS FOR MANAGING PHOTOPHOBIA AND MIGRAINE PHOTOPHOBIA

CROSS-REFERENCE TO RELATED APPLICATIONS

This application is the national phase of International Application No. PCT/US2016/038107, filed Jun. 17, 2016, which claims priority under 35 U.S.C. § 119(e) to U.S. Provisional Application Ser. No. 62/336,364, entitled "PHOTOPHOBIA TREATMENT" filed on May 13, 2016, and U.S. Provisional Application Ser. No. 62/182,347, entitled "METHOD AND APPARATUS FOR MANAGING PHOTOPHOBIA, PARTICULARLY PHOTOPHOBIA ASSOCIATED WITH MIGRAINE" filed on Jun. 19, 2015. The entire contents of these applications are incorporated herein by reference in their entirety.

BACKGROUND

Photophobia can be caused by a variety of triggers including, but not limited to, migraine, post-traumatic headache, headache caused by traumatic brain injury, retinitis pigmentosa, Leber's Congenital Amaurosis, retinal degenerative disease, achromatopsia (e.g., either totally colorblind or almost totally colorblind), albinism, night blindness, and cortical blindness. In some cases, a subject presenting photophobia may seek a darkened room to manage symptoms associated with the photophobia. For example, a person suffering from a migraine photophobia may retreat to a dark room until the headache pain subsides.

During a period in a darkened environment, a person exhibiting photophobia may not be able to undertake visual tasks due to the low-light or no-light levels. For some individuals, the period in a darkened environment can be a period of seclusion and may last for an hour or more. In some cases, photophobic episodes may occur repeatedly for an individual during a single day. Accordingly, photophobia can cause significant lifestyle disruptions to an individual.

SUMMARY

Some embodiments provide simple and efficient techniques for managing light sensitivity (photophobia) such as migraine photophobia. A technique may comprise providing for view, by a subject, illumination having a distinct set of illumination parameters (e.g., centered at a specific wavelength within the visible portion of the electromagnetic spectrum and having a specific range of intensities). A technique may include producing the illumination having a distinct set of illumination parameters that is limited to the green portion of the visible spectrum. The illumination may be produced in at least two ways. In a first aspect, the illumination may be produced by a lighting apparatus having an emissive light source that emits illumination having a distinct set of illumination parameters. In a second aspect, one or more filters may be used to transmit illumination having a distinct set of illumination parameters to a subject and to block or suppress radiation not having the distinct set of illumination parameters. In some aspects, a lighting apparatus may include one or more filters, such that the combination of an emissive source and transmissive filter or filters produces illumination having a distinct set of illumination parameters. A technique may include subjecting a person exhibiting photophobia to the illumination until the photophobia has mitigated.

The illumination parameters may include a characteristic wavelength at about 530 nanometers (nm), a full-width-half-maximum (FWHM) bandwidth less than approximately 2 nm in some cases, and a luminance value in a range from approximately 1 candela per square meter ($cd/m^2$) to approximately 70 $cd/m^2$ received by a person. In some cases, the FWHM bandwidth may be as large as 20 nm. In some instances, the central characteristic wavelength may be between 520 nm and 540 nm. In some embodiments, the illumination may be produced such that at least 90% of the illumination energy is provided within ±1 nm of a characteristic wavelength at 530 nm, while essentially all of the remaining illumination energy is provided within a wavelength range extending from 520 nm to 540 nm. An areal illumination having these parameters or a filtering of ambient light to have these parameters may allow a person presenting photophobia to continue functioning (e.g., reading, writing, etc.) until photophobic symptoms subside.

Some embodiments include a method of alleviating discomfort associated with a photophobic episode (e.g., alleviating pain associated with migraine photophobia). A method of alleviating discomfort may include acts of producing green illumination having a characteristic wavelength at about 530 nm and limited to a narrow bandwidth about 530 nm, and illuminating an environment, in which a person suffering from photophobic discomfort is located, with the green illumination. In some cases, illumination having a characteristic wavelength at 530 nm may be produced by filtering broadband radiation from any suitable light source. In some implementations, the filtering may utilize multilayer coatings and/or thin-film interference or resonant cavity structures applied to a substrate. In some cases, filtering structures may be applied to eyeglass lenses that a user may wear to filter natural light or other light.

A method in which a person is subjected to green illumination may include receiving an indication to stop the exposure, and stopping the illumination in response to the received indication. In some embodiments, the received indication may be an automatic indication that a certain period of time has expired. In other embodiments, the indication may be received based on user input. For example, the person suffering from photophobic discomfort, may be prompted, after a certain time has expired, to provide input regarding whether the exposure has been sufficient or whether the discomfort still continues. If the discomfort continues, additional exposure may continue in predetermined time increments prior to subsequent prompting. In some cases, the person may simply activate a switch, button, or other user input device to provide an indication to start and/or stop the exposure.

Illumination having a characteristic wavelength at about 530 nm may be produced using a lighting apparatus comprising, for example, one or more light emitting diodes (LEDs) or one or more laser diodes (LDs). In some implementations, a light source having a characteristic wavelength at 530 nm may comprise a fluorescent, incandescent, laser source, frequency-doubled laser source, halogen, xenon, tungsten halogen, phosphorescent, or photo-luminescent light source, any combination thereof, or any other type of light source. A light source may be incorporated into a lighting apparatus that produces illumination having a characteristic wavelength at 530 nm. The apparatus may be stationary, lightweight, and/or portable. The apparatus may be, for example, a light bulb, a desk lamp, or an apparatus specifically designed to produce illumination at the desired wavelength and having specific illumination parameters. The apparatus may be adapted to illuminate an area for a person suffering from photophobic disorders (e.g., migraine) using the described techniques without significantly disrupting the person's normal daily activities. A person may utilize an apparatus producing illumination having a characteristic wavelength at 530 nm instead of conventional lighting, according to some embodiments. With such illumination, a person may be able to continue his or her daily activities despite even severe photophobic indications.

Some aspects include eyeglasses that can be worn by a person experiencing photophobia, and that transmit illumination having a characteristic wavelength at about 530 nm and block or suppress other wavelengths. The eyeglasses may comprise a frame, a shield, lenses, and at least one narrow-band filter disposed on the lenses. The narrow-band filter may comprise a multilayer interference bandpass filter configured to pass illumination having a characteristic wavelength at 530 nm, where 90% of the energy of the passed illumination is within ±1 nm of 530 nm in some cases, or within ±10 nm of 530 nm in some implementations. In some implementations, a bandpass of the filter may be larger and a characteristic wavelength may differ from 530 nm.

In some embodiments, an apparatus adapted to emit illumination having a characteristic wavelength at about 530 nm may be placed in an environment designed to alleviate migraines, such as a room in which external sounds and lights can be blocked. The room, or at least a portion around a person to be treated, may be darkened when the illumination is delivered to the person. Such a controlled environment may be located in a medical or other treatment facility where a patient may be treated under an attendant's supervision.

Some embodiments relate to a narrow-band light source comprising an optical source configured to emit visible radiation at a characteristic wavelength only in a wavelength range between 510 nm and 550 nm having a bandwidth no larger than 20 nm full-width-half-maximum, and optical components arranged to spread the radiation over an area that is at least one foot in diameter. In some aspects, the optical source may be configured to produce a luminance between approximately 1 cd/m$^2$ and approximately 70 cd/m$^2$ at a specified working distance from the narrow-band light source. In some aspects, the optical source may be configured to produce a luminance between approximately 1 cd/m$^2$ and approximately 5 cd/m$^2$ at a specified working distance from the narrow-band light source. The lower luminance levels may more greatly alleviate migraine symptoms.

In some implementations, the narrow-band light source may be configured as a desk lamp or floor lamp and the specified working distance is between 1 foot and 3 feet. In some implementations, the narrow-band light source may be configured as a ceiling lamp and the specified working distance is between 3 feet and 10 feet.

The optical components may comprise at least one diverging lens. In some aspects, the optical components comprise at least one diffusing optic to homogenize the radiation. In some implementations, the optical components comprise a slab waveguide to distribute the radiation over a larger area.

According to some implementations, the optical source may comprise one or more laser diodes to provide a narrow band of radiation. In some implementations, the optical source comprises one or more light-emitting diodes to provide a less expensive source of radiation. In some aspects, the optical source comprises phosphor or fluorescent material that converts shorter wavelength radiation to radiation having the characteristic wavelength, so that a other wavelength radiation sources may be used to produce radiation at about 530 nm.

The narrow-band light source may further comprising a power supply, which may comprise a power converter and a voltage-controlled current source.

Any of the foregoing aspects and features of a narrow-band light source may be included in an embodied narrow-band light source.

Some embodiments relate to a narrow-band light source comprising an optical source configured to emit visible radiation at a characteristic wavelength only in a wavelength range between 510 nm and 550 nm and with a luminance between approximately 1 cd/m$^2$ and approximately 70 cd/m$^2$ at a specified working distance from the narrow-band light source. A bandwidth of the visible radiation may be no larger than 20 nm full-width-half-maximum. In some implementations, a bandwidth of the visible radiation may be no larger than 30 nm full-width-half-maximum. In some implementations, a bandwidth of the visible radiation may be no larger than 40 nm full-width-half-maximum.

In some aspects, the optical source comprises one or more laser diodes. In some implementations, the optical source comprises one or more light-emitting diodes. According to some implementations, the optical source comprises phosphor or fluorescent material that converts shorter wavelength radiation to radiation having the characteristic wavelength.

The optical components may comprise at least one diverging lens. In some implementations, the optical components comprise at least one diffusing optic. In some implementations, the optical components comprise a slab waveguide.

A narrow-band light source may further comprise a power supply. The power supply may comprise a power converter and a voltage-controlled current source.

Some embodiments relate to narrow-band eyeglasses comprising a frame, two lenses, shielding attached to the frame and arranged to block light that would bypass the two lenses and enter a user's eyes, and optical filters formed on the two lenses and configured to transmit a visible wavelength range only between 510 nm and 550 nm. In some aspects, the transmitted visible wavelength range has a bandwidth no larger than 20 nm full-width-half-maximum. In some implementations, the luminance of the transmitted visible wavelength is no greater than 70 cd/m$^2$ for either daylight or a standard lit room. In some implementations, the luminance of the transmitted visible wavelength is no greater than 5 cd/m$^2$ for either daylight or a standard lit room.

In some aspects, the optical filters may comprise multi-layer coatings to obtain a desired bandwidth. In some implementations, the optical filters may comprise multi-layer dielectric bandpass interference filters to obtain a narrow bandwidth. In some aspects, the optical filters may comprise metal-dielectric multi-layer blocking filters to attenuate visible radiation. In some implementations, the optical filters may comprise colored glass as a low-cost filter material. In some implementations, the optical filters may comprise optical attenuators to reduce the transmitted radiation to a level that alleviates headache pain. In some aspects, the narrow-band eyeglasses may further comprise microchannels formed in the two lenses that limit the acceptance angle of light passed by the two lenses, so that wavelengths outside of a desired transmission band will not enter the wearer's eyes.

Some embodiments relate to a method comprising acts of providing an enclosed environment for a subject, blocking at least red and blue visible radiation from the enclosed environment, and lighting the enclosed environment with radiation at a characteristic wavelength only in a wavelength range between 510 nm and 550 nm. In some aspects, the radiation may have a bandwidth no larger than 20 nm full-width-half-maximum. In some implementations, the method may comprise producing a luminance between approximately 1 cd/m² and approximately 70 cd/m² at a location of the subject. In some implementations, the method may comprise producing a luminance between approximately 1 cd/m² and approximately 30 cd/m² at a location of the subject. In some implementations, the method may comprise producing a luminance between approximately 1 cd/m² and approximately 10 cd/m² at a location of the subject. In some implementations, the method may comprise producing a luminance between approximately 1 cd/m² and approximately 5 cd/m² at a location of the subject. A level of luminance may be selected that allows the user to carry out some functions (e.g., reading, typing), while also alleviating headache pain or other ailment symptoms.

The foregoing summary is provided as an introduction and is not intended to be limiting.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 6A depicts eyeglasses that may include narrow-band filters according to an embodiment;

FIG. 6B depicts a cross-section of an eyeglass frame and lens according to an embodiment;

FIG. 7A depicts a cross-section of a substrate and filter according to an embodiment;

FIG. 7B depicts a cross-section of a substrate and filter according to an embodiment;

DETAILED DESCRIPTION

I. Introduction

Figure 1:
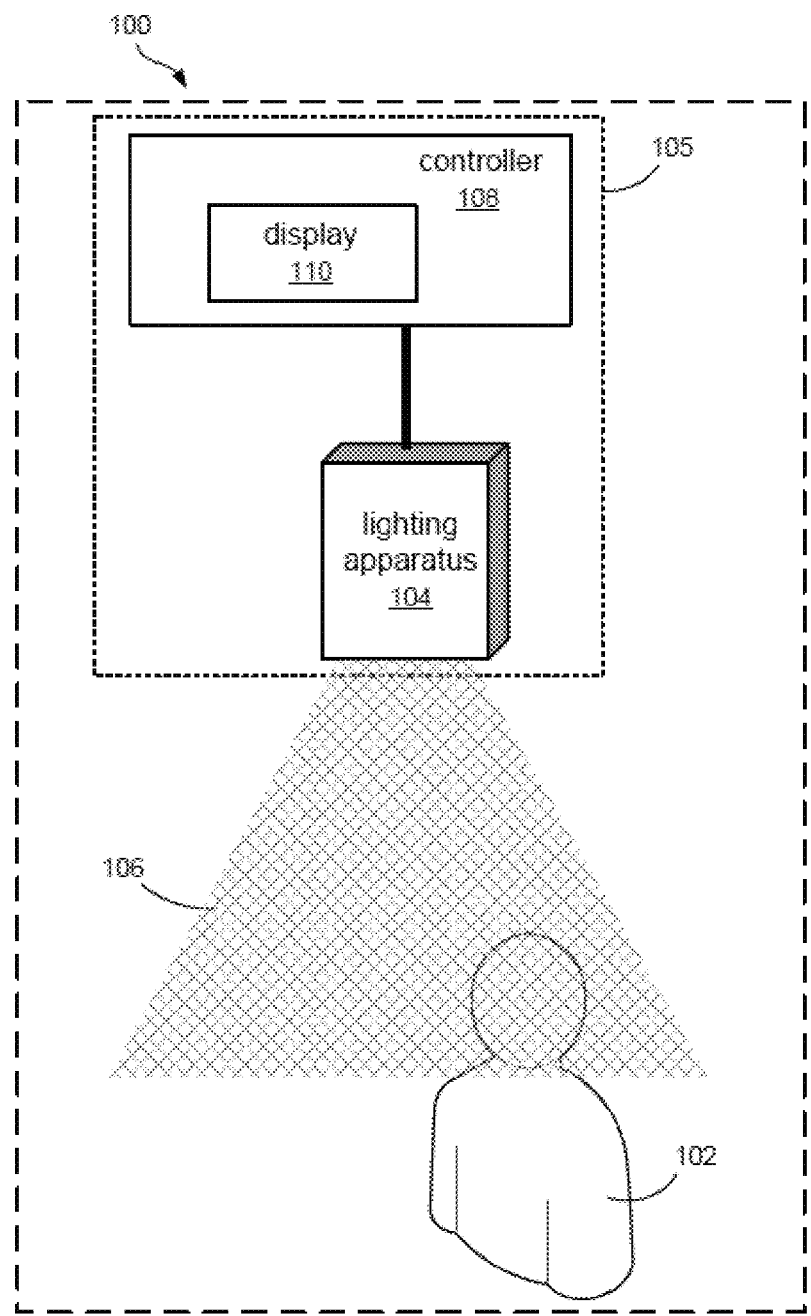
FIG. 1 is a schematic illustration of an exemplary environment in which some embodiments may be implemented.

The inventor has unexpectedly and surprisingly discovered that photophobia may be alleviated under particular lighting conditions. Normally, exposure to the majority of the visible portion of the electromagnetic spectrum does not improve or can exacerbate photophobic symptoms (such as migraine pain). Accordingly, an individual suffering photophobic discomfort may seek a darkened environment in which light levels may be too low for the individual to carry out visual tasks. The inventor has recognized and appreciated that some individuals can experience a reduction in photophobic symptoms under specific lighting conditions that enable the individual to continue visual-related functions. For example, an individual suffering from a migraine may continue visual tasks (e.g., reading, writing, manual tasks, etc.) in an environment illuminated with green light, and may experience alleviation of the migraine. Although the exposure to green light may not terminate photophobic symptoms, the exposure may be sufficient to reduce headache, without causing any known side effects, so that the individual can resume visual functioning. Accordingly, many individuals may no longer experience significant disruptions to their daily activities during photophobic episodes.

The inventor has unexpectedly and surprisingly discovered that illumination having a characteristic wavelength at about 530 nm and limited to the green region of the visible spectrum may alleviate photophobia in some individuals. The term "characteristic wavelength" refers to a central and/or peak wavelength of the light source. For example, the inventor has measured a reduction in pain associated with migraine in a plurality of individuals that are exposed to narrow-band green illumination at low luminance values. Thus, some embodiments provide simple, effective, non-invasive, and cost-effective techniques for providing illumination at 530 nm wavelength to a subject experiencing photophobia. The illumination may have a luminance value at the subject's eyes in a range between approximately 1 candela per square meter (1 cd/m²) to approximately 70 cd/m², according to some embodiments. In some embodiments, the light having a characteristic wavelength at 530 nm may be produced so that 90% of the illumination energy is provided within at most a 2 nm bandwidth centered at a 530 nm, while essentially all of the remaining illumination energy is provided in a range from 520 nm to 540 nm. In some cases, the characteristic wavelength may be between approximately 520 nm and approximately 540 nm. In some embodiments, the light may be produced so that 90% of the illumination energy is provided within at most a 20 nm bandwidth about its characteristic wavelength.

Some embodiments include a light source that may be incorporated into a lighting apparatus. The light source may be capable of emitting light having a characteristic wavelength of 530 nm and specific illumination parameters relating to bandwidth and luminance. In some cases, the light source may comprise one or more light emitting diodes (LEDs) or one or more laser diodes (LDs) or a combination thereof. Additional non-limiting examples of a light source include a fluorescent source, an incandescent source, a laser source, a frequency-doubled laser, a halogen source, a xenon source, a tungsten halogen source, a photo-luminescent source, a phosphorescent source, a candle-luminescent source, an electro-luminescent source, a crystallo-luminescent source, a cathodoluminescent source, a thermo-luminescent source, and any combination thereof. A light source may be incorporated into a lighting apparatus and configured to produce between approximately 1 cd/m$^2$ to approximately 3500 cd/m$^2$ of illumination having a characteristic wavelength of 530 nm (e.g., to illuminate a room).

In some implementations, a light source may comprise a conventional light source and narrow-band optical filters that pass light having a characteristic wavelength of 530 nm. The filters may be placed over a housing containing the light source. In some implementations, a phosphor (e.g., ZnS:Cu or $Y_3Al_5O_{12}$:Ce) and/or fluorescent material may be used to convert shorter wavelength radiation emitted by a source to green illumination, which may be subsequently filtered. In some embodiments, narrow-band optical filters may be placed on eyeglasses to filter natural (solar) or artificial (incandescent, fluorescent, LED, or laser) light.

Results from several studies are included that show the effectiveness of green light over other wavelengths for alleviating photophobia.

II. Managing Photophobia

The described devices and techniques may be used to manage and/or alleviate photophobia having different causes, e.g., migraine without aura, migraine with aura and retinal migraine, post-traumatic headache, headache caused by traumatic brain injury, and other types of headaches. Furthermore, light having a characteristic wavelength of about 530 nm may be used to alleviate migraine in persons that have normal vision and in persons suffering from ocular diseases such as retinitis pigmentosa, Leber's Congenital Amaurosis, retinal degenerative disease, achromatopsia (e.g., either totally colorblind or almost totally colorblind), albinism, night blindness, and cortical blindness. In some cases, light having a characteristic wavelength of about 530 nm may be used to alleviate symptoms associated with generalized anxiety disorders, such as post-traumatic stress disorder (PTSD), obsessive compulsive disorder (OCD), and panic disorder. In some cases, light having a characteristic wavelength of about 530 nm may be used to alleviate symptoms associated with Lyme disease. Photophobia triggered by other causes may also be alleviated by exposing a subject to green light having distinct illumination parameters.

Migraine is a common, sometimes chronic, and potentially incapacitating condition that affects significant number of people, and can trigger severe photophobia. Migraine is typically exacerbated by light and may, in some cases, even be triggered by light. Migraine causes a severe, throbbing headache associated with nausea and other neurological symptoms such as weakness, loss of vision, or difficulty speaking. Migraine may also be accompanied by psychological symptoms such as fatigue and depression. In some cases, migraine may be associated with an increased risk of stroke. Migraine headache can render migraine sufferers dysfunctional as they are forced to quit their normal daily tasks and seek reprieve in darkness.

Because of the repetitiveness and frequency of migraine, sufferers typically endure a significant hardship as a result of spending a large amount of time in solitude during working hours or at times which would otherwise be spent in social activities.

Many migraine sufferers not only experience severe physical discomfort, but are often affected by migraine in other ways. One of the most serious implications of migraine is photophobic intolerance to light. As a result, a person suffering a migraine attack often needs to interrupt his or her daily activities and retreat to an area with little or no lighting. Migraine therefore can cause disruption of work and other normal activities. A person's productivity during migraine may be severely compromised, and they may not be able to perform visual tasks at all. This is particularly exacerbated by a typical increase of severity and frequency of migraine attacks with person's age. Because many migraine sufferers continue experiencing recurring migraine attacks for years, their lives may become significantly disrupted due to their need to spend extended hours in darkness and solitude.

Although migraine is one complication associated with photophobia, it and other conditions associated with photophobia may be managed, and in some cases alleviated, using the devices and techniques described below.

III. Devices and Techniques

FIG. 1 illustrates schematically an exemplary lighting environment 100 in which some embodiments may be employed. A person 102 experiencing photophobia may find reprieve using the described apparatus and techniques. The term "person," "patient," "user," "individual," and "subject" may be used interchangeably herein to denote a human subject who suffers from or presents a photophobic episode. As shown in FIG. 1, a lighting environment 100 may comprise a lighting instrument 105 capable of producing illumination 106 having a characteristic wavelength of 530 nm and a narrow-bandwidth limited to the green portion of the spectrum. The illumination may not include light from other portions of the visible spectrum. The instrument 105 may comprise a lighting apparatus 104, which produces the illumination 106, a controller 108, and may further include a display 110. The controller may drive the lighting apparatus, and the display may provide a visual indication (e.g., text or graphics) for operation of the instrument 105. The instrument 105 may illuminate an area in which the person 102 experiencing photophobia is located.

The lighting apparatus 104 may comprise any suitable light source, for example, one or more LEDs, laser diodes, or a combination thereof. The light source may, in some embodiments, comprise incandescent, fluorescent, halogen, laser, luminescent source, phosphorescent, or any other type of light source or a combination of light sources that can be arranged to produce illumination 106 having a characteristic wavelength of 530 nm. The illumination 106 may be continuous, but may comprise pulses in some embodiments. The pulses may be repeated rapidly on a time scale, such that the light appears continuous to the person 102. It should be appreciated that the techniques described herein are not limited to any specific type of light source capable of producing illumination 106 having a characteristic wavelength of approximately 530 nm.

In some embodiments, a light source (e.g., incandescent, fluorescent, LED, laser, or other type) may produce light having a broader wavelength range than useful for a lighting environment 100. In such embodiments, the lighting apparatus 104 may include one or more optical filters configured to shape a spectral distribution of the illumination 106. For example, the optical filters may selectively transmit light of a desired wavelength (530 nm) while attenuating light at other wavelengths. In this way, various types of light sources may be used for a lighting environment 100.

A lighting instrument 105 may be portable or stationary, and may be of any suitable size, design and type of operation. In some embodiments, a lighting instrument 105 may not include a display, and the controller may comprise a power source or connection to a power source and on/off switch. In some implementations, lighting instrument 105 may comprise a battery-powered lighting apparatus that is portable, so that a user may conveniently use the instrument in different settings. The battery may be rechargeable or replaceable. Lighting instrument 105 may have any suitable shape. In some embodiments, a lighting apparatus 105 may be incorporated into a lamp, e.g., a ceiling lamp, an office desk lamp, or other lamp that may be located in a home, office or other setting. In some implementations, lighting apparatus may be incorporated into a head-mounted or wearable device, such as eye glasses, a hat, a visor, a mask, or any other suitable device, and configured to shine light in a direction that the user looks. The illumination 106 may allow a user to continue performing his or her daily activities in an area illuminated by the light. In some cases, the lighting apparatus 104 may be incorporated into a laptop, tablet, mobile phone or any other instrument to illuminate at least a portion of the instrument's user interface (e.g., to illuminate a keypad).

Operation of lighting apparatus 104 may be controlled via a controller 108, which may be incorporated as a part of a packaged instrument 105. Though, in some embodiments, controller 108 may be a separate component from the lighting apparatus that is connected by a flexible cord or wireless link. In some embodiments, controller 108 may be a remote controller. Though, it should be appreciated that the techniques described herein are not limited to any particular way of controlling operation of lighting apparatus 104.

Controller 108 may include circuitry configured to control operation of lighting apparatus, and may be implemented in any suitable manner. For example, controller 108 may control the flow of electrical power to the light source to start and stop the illumination 106. In some cases, the controller may connect to and monitor output from one or more sensors (e.g., thermal and/or optical sensors) configured to sense optical output of and/or temperature of the lighting apparatus 104. In some embodiments, controller 108 may include any suitable processor, such as, for example, a microprocessor, a digital signal processor (DSP) or a microcontroller. In some implementations, controller 108 may be used to control a wavelength, intensity, and other parameters of illumination 106, such as a pulse rate, a pulse width and a duty cycle, as well as duration of delivery of the illumination. In some embodiments, controller 108 may receive input with respect to operating parameters of instrument 105. For example, the controller 108 may include one or more control buttons, knobs, or switches. In some implementations, the controller may include a keypad.

Instrument 105 may include a display 110 connected to controller 108, in some embodiments. The display 110 may, or may not, be packaged with the controller. The display may comprise a user interface (e.g., touch screen). A user interface may be displayed by controller 108 on the display 110 and provide information associated with operating parameters of the instrument 105. A user may input data, via the display or other controls, to set and adjust illumination parameters. In some cases, display 110 may be configured to display information on different modes of operation of instrument 105, and the controller 108 may receive input from the user indicating a selection of a mode. In some embodiments, a user or attendant may input or select data representative of the user's condition. The user's conditions may comprise his or her age, a type of photophobic episode, severity and frequency of discomfort. The controller 108 may then automatically select parameters for illumination 106, and initiate illumination based on the selected parameters.

Additionally or alternatively, display 110 may be configured to display other information that may be used to control operation of instrument 105. For example, display 110 may display information relevant to a distance between lighting apparatus 104 and a user's location. For example, an operator of the instrument 105 may select a distance from a set of distances displayed on display 110. In some embodiments, the light emitting device may be capable of automatically determining the distance to objects and may thus dynamically adjust operating parameters of the light source based on a distance to a person or object near the person (e.g., a desk). Based on a determined distance between the lighting apparatus 104 and a user 102, the controller may select a power level at which to drive the light source.

In some implementations, the lighting apparatus 104 may comprise a display associated with a personal electronic instrument (e.g., a computer, smart phone, or head-mounted display). For example, the lighting apparatus may be operated remotely by an application running on a personal electronic instrument. In such an embodiment, there may not be a separate display 110, and the controller may comprise a processor (e.g., microcontroller, control circuitry, microprocessor, field-programmable gate array, etc.) of the instrument 105.

The controller 108 may cause lighting apparatus 104 to emit illumination 106 having a characteristic wavelength of 530 nm in accordance with the selected or entered operating parameters. The illumination 106 may be delivered to a person 102 and/or surrounding environment in any suitable way. For example, the lighting apparatus 104 may be positioned with respect to person 102 so that illumination 106 is delivered indirectly or directly to the person's eyes. An arrangement of lighting apparatus 104 with respect to person 102 may be adjustable.

In some embodiments, controller 108 may include memory that may be connected to a processor. The memory may store, for example, operating parameters and information associated with the operating parameters for controlling operation of the instrument 105. The memory may also store computer-readable instructions that, when executed by the processor, may instruct the instrument 105 to produce light in accordance with the operating parameters.

Environment 100 may comprise an enclosed space adapted to block or reduce light from sources other than lighting apparatus 104. In some embodiments, environment 100 comprises a room into which one or more individuals experiencing photophobia may enter. In some implementations, environment 100 comprises a waiting room or treatment room at a clinical facility. In some implementations, environment 100 comprises an office at a commercial facility. In some cases, environment 100 comprises a residential room. According to some embodiments, any of the foregoing environments may be configured with lighting apparatus 104. Any of the foregoing environments may further be configured with conventional lighting, so that the environment can be lit with conventional lighting for individuals not experiencing photophobia. The same environment may alternatively be lit with narrow-band illumination when an individual experiences photophobia, e.g., by switching from one lighting source to the other.

Figure 2:
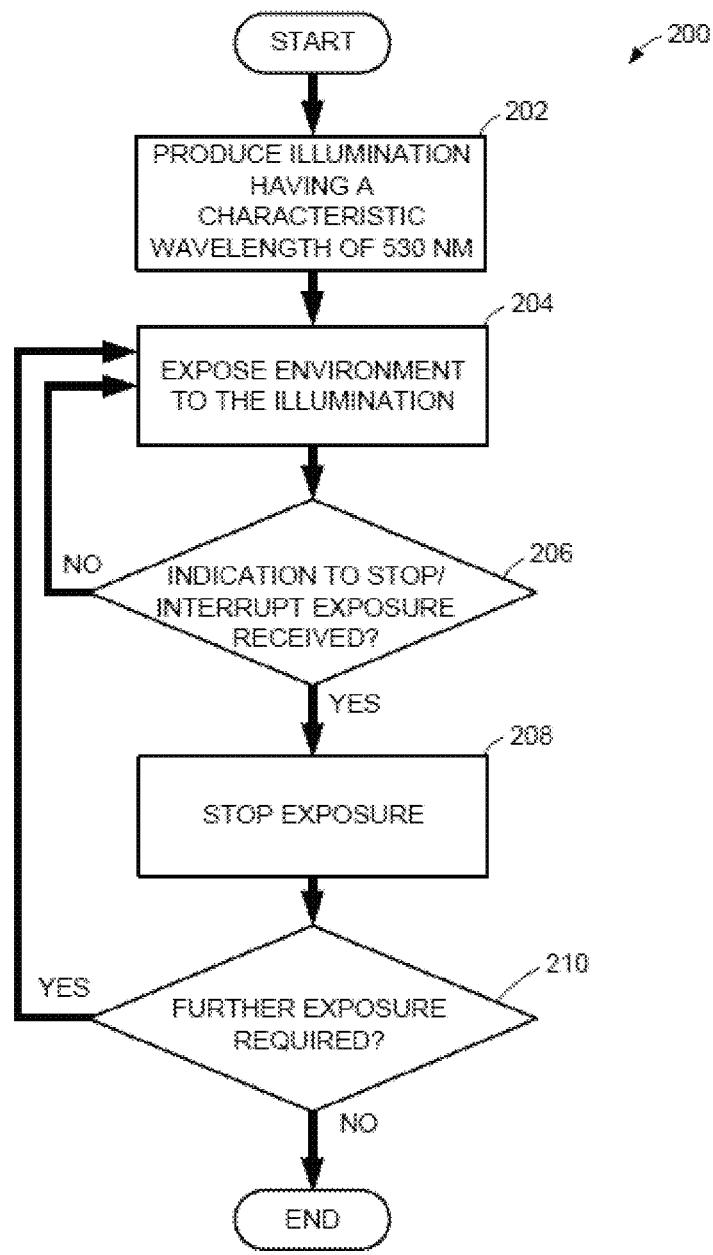
FIG. 2 depicts acts of a process for mitigating photophobia, in accordance with some embodiments.

FIG. 2 illustrates just one exemplary process 200 of mitigating photophobia (e.g., due to migraine) using light having a characteristic wavelength of 530 nm and limited to a narrow bandwidth in the green portion of the visible spectrum. Process 200 may begin at any suitable time for a person exhibiting photophobia. The process may comprise producing (act 202) illumination 106 having a characteristic wavelength of 530 nm. In some embodiments, the characteristic wavelength may have a value between approximately 520 nm and approximately 540 nm. The light may be produced using an instrument 105, as described in connection with FIG. 1.

A process 200 may further include exposing (act 204) an environment and/or person exhibiting photophobia to the illumination having a characteristic wavelength of 530 nm. The act of exposing may comprise controlling the luminance of the light at the location of the person to be between approximately 1 cd/m$^2$ and approximately 70 cd/m$^2$. It should be appreciated, however, that embodiments are not limited to any specific luminance value. In some embodiments, the luminance at the light source may range from approximately 1 cd/m$^2$ to approximately 3500 cd/m$^2$. Though, it should be appreciated that other intensity values may be used, as embodiments are not limited in this respect. The luminance value at the light source may be selected based on a distance between the light source and the person. In some embodiments, the luminance value at the light source may be selected based on a type of the light source. For example, the luminance projected from the lighting apparatus to an area viewed by the user (e.g., a desk top) may be different depending upon a divergence of the illumination from the lighting apparatus, for example. The luminance may also be selected based on the person's physiological and psychological characteristics, and any other factors.

In some embodiments, an instrument 105 may be configured to receive one or more inputs indicating a beginning and an end of exposing (act 204). For example, a process 200 may comprise a conditional act of determining (act 206) whether an indication to stop exposure has been received. If an indication to stop exposure has been received, the process may continue to stopping (act 208) the exposure. In some embodiments, the process 200 may then end. If an indication to stop exposure has not been received, the process may continue exposing (act 204) the environment to the illumination.

In some embodiments, a process 200 may include an interruption in exposure. For example, after stopping (act 208) the exposure and before ending the process, a period of time may elapse. The process may further include a conditional act of determining (act 210) whether further exposure has been indicated. If further exposure is required, the process may return to exposing (act 204) the environment. If further exposure is not required, the process may end.

In some embodiments, a person experiencing photophobia may be exposed to illumination having a characteristic wavelength of 530 nm in one or more sessions supervised by a parent, physician, nurse, or other attendant. For example, a child experiencing a severe migraine or an adult recovering in a hospital may be subjected to narrow-band illumination to help alleviate discomfort. A number and duration of sessions and illumination parameters (e.g., luminance, wavelength) may be selected depending on a severity of photophobia for the person. In some cases, a duration of the session may be predefined based on the severity. For example, the lighting apparatus 104 may be controlled by controller 108 to emit the illumination for a certain amount of time after it is started and then to automatically stop after the predefine time. In some implementations, the duration of a session may be controlled by an operator of the lighting apparatus 104.

In some embodiments, feedback may be collected from a person in an environment 100 lit by the narrow-band illumination 106. It may be determined, based on the person's feedback, whether to terminate, adjust illumination parameters, or continue the exposure. In some embodiments, the parameters may also be adjusted automatically by a controller 108 in response to the person's feedback. In embodiments where the light emitting device is controlled by an operator, the operator may execute any changes to the illumination, e.g., manually adjust the operating parameters of the lighting instrument 105.

Figure 3:
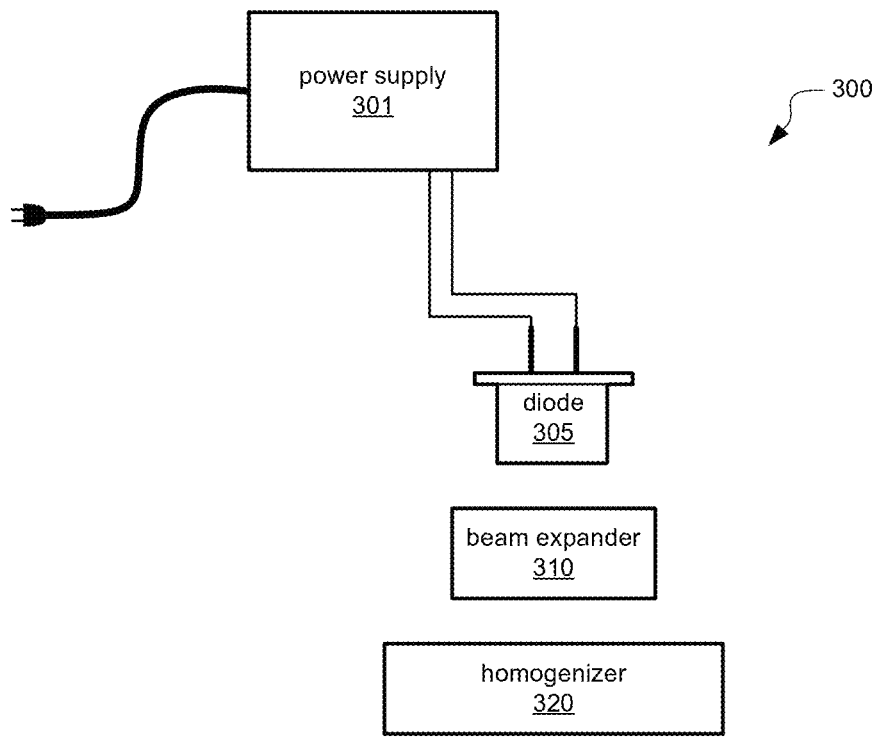
FIG. 3 illustrates a lighting instrument according to an embodiment.

Referring now to FIG. 3, one embodiment of a lighting instrument 300 that produces narrow-band illumination having a characteristic wavelength at 530 nm is depicted. In some embodiments, a full-width-half-maximum value (FWHM) of the produced illumination may be less than or equal to about 1.7 nm. The lighting instrument 300 may comprise a power supply 301, a laser diode 305, a beam expander 310, and a homogenizer 320. The power supply may receive AC power in some embodiments, as depicted in the drawing, or may receive DC power (e.g., from a battery) in other embodiments, and may provide a DC current to the laser diode. The light source may comprise a laser diode 305, a frequency-doubled laser diode, or high-brightness LED that emits radiation in a narrow band centered at 530 nm. Semiconductor laser diodes fabricated from GaN/InGaN materials have been found to emit up to 100 mW of power continuously at about 530 nm. The beam expander 310 may introduce beam divergence into the light emitted from the laser diode, and the homogenizer 320 may diffuse and randomize the beam from the beam expander. Light from the homogenizer may be used to illuminate an environment. In some embodiments, the power supply may drive more than one laser diode or LED. In some implementations, the lighting instrument 300 may be packaged into a form compatible with conventional residential and commercial light-bulb receptacles, so that lighting instrument 300 screws into a receptacle and is powered by conventional alternating current.

Figure 4A:
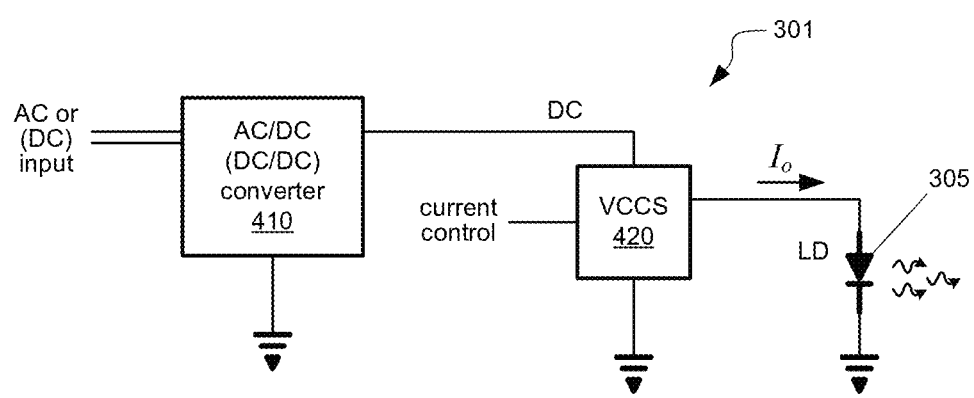
FIG. 4A illustrates a power supply according to an embodiment.

FIG. 4A depicts one embodiment of a power supply that may be used to operate a narrow-band lighting instrument. According to some embodiments, the power supply comprises a power converter 410 coupled to a voltage-controlled current source 420. The power converter 410 may receive AC or DC input of a first voltage specification. The power converter may comprise switched-mode power conversion circuitry configured to convert the AC or DC input to at least one DC voltage output. An example of switched-mode power conversion circuitry can be found in compact chargers for mobile phones.

The power supply 401 may further include a voltage-controlled current source (VCCS) 420 that may receive a DC output voltage from the power converter 410, and provide an output current to drive at least one laser diode 305. According to some embodiments, the output current $I_o$ is fixed, and there may be different power supplies 401 each having a different fixed output current to produce illumination with different luminance values. In some implementations, the output current is variable and may be adjusted by a user to adjust the output intensity from the laser diode or LED. In some embodiments, current control may be achieved by a user rotating a potentiometer that adjusts an output voltage from a resistive voltage divider. In some embodiments, current control may be obtained by transmitting (in a wired or wireless link) a digital signal to the VCCS. The VCCS may include a digital-to-analog converter that converts the received digital signal to an analog voltage that is used to control the current output from the VCCS. In some implementations, VCCS may comprise an operational amplifier and/or current buffer. According to some embodiments, the VCCS 420 may be packaged in a same assembly with the power converter.

Figure 4B:
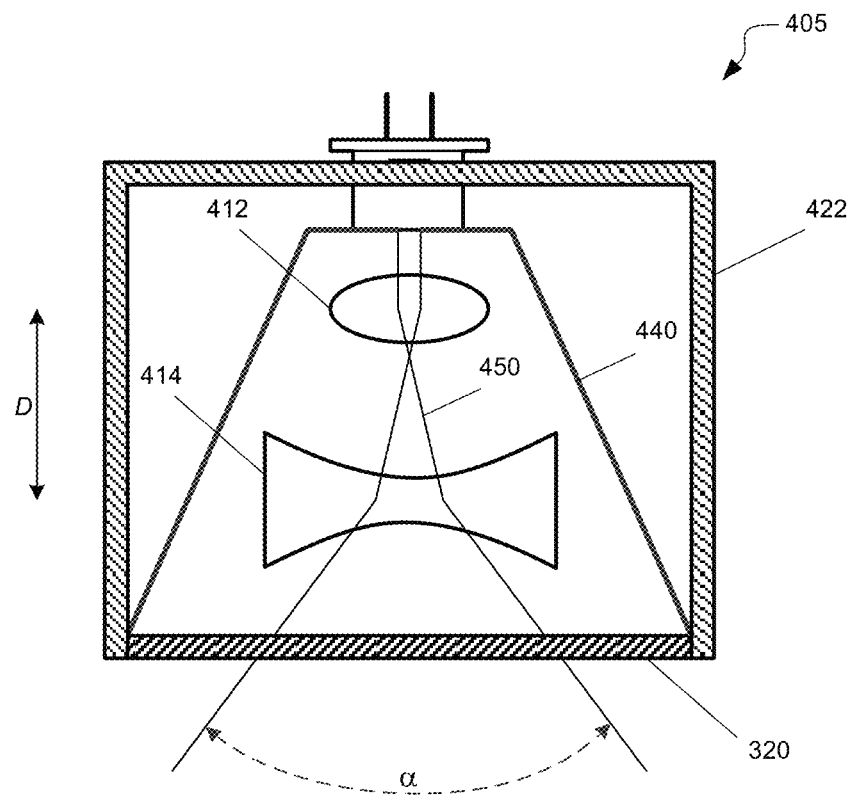
FIG. 4B illustrates a lighting apparatus according to an embodiment.

One embodiment of a narrow-band lighting apparatus 405 is depicted in FIG. 4B. A narrow-band lighting apparatus may comprise an outer housing 422 to which is mounted a laser diode 305 or LED, a reflector 440, at least one lens 412, 414, and a homogenizer 320. As noted above, the laser diode may comprise a GaN-based semiconductor laser or high-brightness LED emitting radiation at 530 nm with a narrow spectral bandwidth (e.g., less than about 2 nm in some cases, less than 20 nm in some cases). In some implementations, there may be more than one diode in a narrow-band lighting apparatus 405. A laser diode may have emission bandwidths on the order of 2 nm or less. Additionally, the spectral bandwidth of a laser diode may be narrowed to well below 1 nm by incorporating distributed feedback structures in or adjacent to the active region of the laser diode. According to some embodiments, a laser diode 305 may output radiation at 530 nm at powers up to about 100 mW. The light output power from the laser diode may be controlled by the amount of current applied to drive the laser diode. In some embodiments, an output from one or more LEDs may be filtered with narrow-band optical filters (e.g., a laser-line filter) to produce narrow-band illumination having a characteristic wavelength of 530 nm.

An output beam 450 may be incident on a focusing lens 412 or diverging lens (not shown), according to some embodiments. The focusing lens may be a small double-convex lens with a short focal length. For example, the focusing lens 212 may comprise a 3 mm diameter lens with a 3 mm focal length (available from Edmund Optics, part No. 49-181). After passing through the focusing lens 412, the beam may come to a focus (or diverge for a diverging lens) and then begin diverging as it travels to a diverging lens 414. The diverging lens may be located a distance D from the focusing lens, wherein D is greater than a focal length of the focusing lens 412.

The diverging lens may be a double-concave lens that introduces further divergence into the beam 450, such that the beam emerges from the diverging lens with a divergence angle α, as depicted in the drawing. The diverging lens may also have a short focal length. An example of a diverging lens may be a double-concave lens having a 6 mm diameter and a −6 mm focal length (also available from Edmund Optics, part No. 47-914). In some embodiments, the focusing lens and diverging lens may be formed from a polymer, or from a glass. When formed from a polymer, the focusing lens and/or diverging lens may include embedded scatterers (e.g., reflective particles or small particles having a refractive index different from the material used to form the lens) to help randomize and further disperse the beam from the diode.

The focusing lens 412 and diverging lens 414 may have anti-reflection coatings in some embodiments, so as to reduce back-reflected light to a laser diode 305. Reflections back to the laser diode may destabilize the laser diode. To prevent optical feedback to the laser diode, an optical isolator (not shown) may be placed between the laser diode 305 and focusing lens 412.

The beam 450 emerging from the diverging lens 414 may pass through a homogenizer 320. The homogenizer may comprise one or more films or substrates configured to further scatter and randomize the beam. According to some embodiments, the homogenizer spoils spatial phase coherence of a laser beam. In some embodiments, the homogenizer may comprise a polymer sheet impregnated with scatterers so as to disperse the beam 450. In some implementations, the homogenizer 320 may comprise prism sheets or surface-structured sheets, similar to those used in LED/LCD displays. A surface-structured sheet may include scattering features imprinted or formed at one or more surfaces of the sheet. A surface-structured sheet may comprise a phase randomizer the includes random, micron-sized or sub-micron-sized, phase steps distributed randomly across the sheet. In some embodiments, the homogenizer may comprise any combination of the following: one or more scatter sheets, one or more prism sheets, and one or more surface-structured sheets.

The diode 305, lenses 412, 414, and homogenizer 320 may be substantially surrounded on a back side by a reflective shell 440. The reflective shell may help homogenize the output beam and redirect any back-reflected radiation out of the lamp assembly in the forward direction. The reflective shell may comprise a molded polymer coated with a reflective metallic and/or dielectric coating.

In some embodiments, the lighting apparatus 405 shown in FIG. 4B may further include, in a same package, the power supply circuitry depicted in FIG. 4A. For example, power supply circuitry may be mounted to the housing 422 and connected to the laser diode 305. In some implementations, the housing 422 may be approximately the size of a standard household light bulb, and may further include a screw-in contact, so that a lamp assembly including on-board power-supply circuitry may screw into a conventional light receptacle.

The arrangement of optical lenses 412, 414 in the lighting apparatus 405 may determine an output luminous intensity from the lamp. In general, the luminance depends upon several parameters including, but not limited to, divergence angle β of the beam from the diode, diameter w of the beam from the diode, the diode power $P_1$, focal length $f_c$ of the focusing lens, focal length $f_d$ of the diverging lens, and distance D between the two lenses. Table 1 provides a list of parameters for one example of a lamp assembly in which a ceiling-mounted lamp would provide up to a maximum of about 55 cd/m² over an area of a standard work desk (e.g., an area of about 2.5 square meters).

TABLE 1

| Lamp Parameters | |
| --- | --- |
| $P_1$ | 100 mW |
| β | 1 degree |
| w | 1 mm |
| $f_c$ | 3 mm |
| $f_d$ | −6 mm |
| D | 9 mm |

Because a diode may have an adjustable output power, the luminance could be varied from low levels (e.g., less than 1 cd/m²) to the maximum output. In some embodiments, a power supplied to the diode may be fixed at one of a set of discrete values, so that each lighting apparatus 405 provide a discrete luminance value. A laser diode configured in the lighting apparatus 405 can deliver a luminance value between approximately 1 cd/m² and approximately 55 cd/m². In some cases, more than one laser diode 305 or LED may be used in a lighting apparatus 405.

Commercial laser diodes and LEDs may be packaged with optical components to form a narrowly diverging or collimated beam. For example, a micro-lens or other lensing structure may be formed or attached at an exit surface of the diode. Without these collimating optical components, the beam from a diode may naturally diverge in an elliptical pattern. According to some embodiments, a diode may be used without collimating optical components. This may reduce the cost of the diode, and may eliminate the need for a focusing or diverging lens 412. In some embodiments, a subsequent diverging lens 414 may or may not be used.

Figure 5:
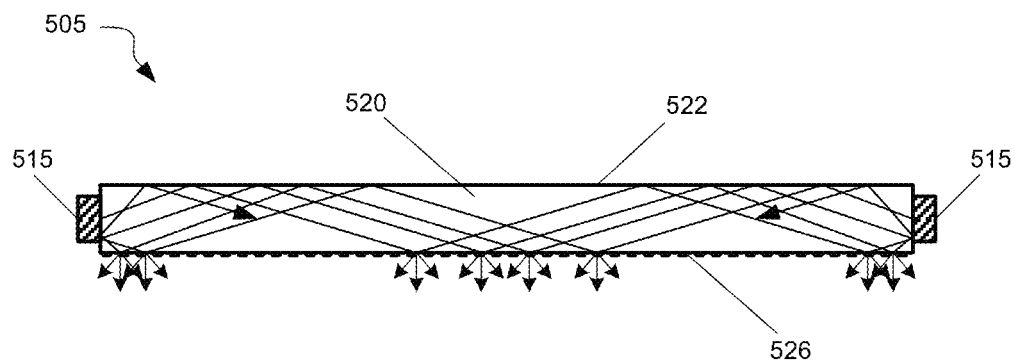
FIG. 5 illustrates a lighting apparatus according to another embodiment.

FIG. 5 depicts another embodiment of a lighting apparatus 505. In this embodiment, naturally diverging output from at least one laser diode or LED chip 515 (e.g., a chip having no collimating optical elements) illuminates a diffusive slab waveguide 520. The slab waveguide may comprise a polymer sheet with surface structures on an emissive surface 526 and reflective coatings 522 on the other surfaces. Light from the chips 515 may multiply reflect inside the slab and be extracted from the emissive surface. Such slab waveguides are common to edge-lit LCD displays, and may provide a distributed light panel that can measure up to more than a meter in length on each side. In some embodiments, diverging and/or scattering optics may be placed between the chip 515 and the slab waveguide 520 to further disperse the beam from the diode chip before entering the slab waveguide.

When multiple diodes (LDs or LEDs) or diode chips are used, optical feedback that destabilizes a diode may be acceptable in some embodiments, provided the feedback does not perturb the laser diode's emissive wavelength outside of a 20 nm bandwidth, for example, centered at 530 nm. Random intensity variations among multiple diodes due to optical feedback may effectively cancel each other so as to give the appearance of a substantially uniform brightness light source. Therefore, optical isolation may not be needed in some embodiments.

In some implementations, the embodiments of lighting apparatus depicted in FIG. 3, FIG. 4B, and FIG. 5 may be arranged to spread the produced green radiation over an area that is at least one foot in diameter at a specified working distance from the lighting apparatus. In other implementations, the lighting apparatus may be configured to spread the produced green radiation over larger areas.

Other methods of producing narrow-band illumination having a characteristic wavelength at 530 nm are also contemplated by the inventor. Some methods may include passive filtering of ambient or solar light. According to some embodiments, eyeglasses 600, as depicted in FIG. 6A, may be worn by a person experiencing photophobia, and may be used to block or reduce visible radiation at wavelengths other than a narrow band of wavelengths at 530 nm and transmit radiation in a narrow band having a characteristic wavelength of 530 nm.

Eyeglasses 600 may comprise a frame 610 and lenses 630 that include narrow bandpass optical filters and/or other optical filters. In some implementations, the eyeglasses may include a shield 615 attached to the frame, as depicted in FIG. 6B. The shield may be opaque and configured to block radiation from the user's eyes that would otherwise bypass the lenses 630 and enter the user's eyes. The shield may be formed of a polymer, elastomer, fabric, composite, or any other suitable material. The shield may be flexible and conform to contours of the user's face.

Lenses 630 may comprise multi-layer structures, as depicted in FIGS. 7A-7B. According to some embodiments, lenses 630 may be formed of a glass or polymer substrate 732, and include a multi-layer filter assembly 736 formed on at least one side of the substrate. In some implementations, the substrate 732 may include microchannels 734 extending all or part way through the substrate. The microchannels may limit the acceptance angle of radiation passing through the substrate 732. In some embodiments, the microchannels may be formed by etching, piercing, or imprinting. In some embodiments, the microchannels may comprise opaque walls surrounding each channel, e.g., a mesh filled with a resin or a black matrix. In some cases, the walls of the microchannels may be plated with a metal after forming channels.

Light passing through the substrate may be filtered by a multi-layer filter assembly 736. The multi-layer filter assembly may include alternating layers of high and low index material, and may further include at least one layer of colored glass. The high-index material may be zinc sulfide (ZnS), and the low index material may be cryolite ($Na_3AlF_6$). The alternating layers may comprise at least one dielectric interference filter designed as a narrow bandpass interference filter for 530 nm. There may be multiple dielectric interference filters spaced apart by spacing layers. The multi-layer filter assembly 736 may further include at least one metal-dielectric blocking filter to suppress wavelengths greater than about 530 nm. Metal layers may comprise chrome, aluminum, or any other suitable metal. In some implementations, the colored glass may suppress wavelengths shorter than about 530 nm. The metal-dielectric blocking filters may be oriented on a side of the filter assembly 736 away from the user's face to help prevent solarization of the colored glass or dielectric layers.

Because interference filters are angle-sensitive, microchannels 734 may be formed in the substrate 732 to help suppress off-axis and out-of-band radiation that might otherwise pass through the lenses 630. The microchannels may be formed as a black matrix and limit the acceptance angle of light that passes through the lenses to ±15 degrees or less.

In some embodiments, lenses 630 may not include microchannels. In some implementations, substrate 732 may comprise a uniform polymer or glass. In some cases, substrate 732 may comprise colored glass that filters at least a portion of the visible spectrum and transmits visible radiation having a characteristic wavelength of about 530 nm. According to some embodiments, lenses 630 may include a first multi-layer filter assembly 735 on a first side of substrate 732 and a second multi-layer filter assembly 737 on a second side of the substrate. The first filter assembly 735 may comprise a metal-dielectric multi-layer blocking filter, and the second filter assembly 737 may comprise at least one multi-layer dielectric bandpass interference filter.

In some implementations, one or both of the first filter 735 and second filter 737 may comprise a single layer of material. For example, the first filter 735 may comprise a short-wavelength filter that blocks light below about 530 nm, and the second filter 737 may comprise a long-wavelength filter that blocks light above about 530 nm. In some cases, one or more filter assemblies may be used, instead of narrow bandpass interference filters, that provide a passband broader than 2 nm FWHM, e.g., a passband up to 20 nm FWHM. To protect the filters and microchannels, an inorganic coating (e.g., an oxide coating) may be formed over the each side of the lenses 630. In some embodiments, one or both of the first filter 735 and second filter 737 may comprise one or more layers of polymer and arranged to transmit radiation having a characteristic wavelength of about 530 nm. Some polymer layers may contain absorptive dyes. Some polymer layers may contain material (e.g., nanoparticles) that increases the average refractive index of the polymer, so that alternating layers of high and low refractive indices can be formed from polymeric layers.

The eyeglasses 600 may be worn by a person experiencing photophobia to help manage the photophobia. In some embodiments, the eyeglasses may include optical attenuation to reduce the filtered light intensity to a suitable range, e.g., between approximately 1 candela per square meter (1 $cd/m^2$) to approximately 70 $cd/m^2$. In some cases, the eyeglasses may be made available in at least two different models with different optical attenuations. A first model would filter sunlight and attenuate the resulting green light to a suitable level within the desired range. A second model would filter standard room light and attenuate may or may not attenuate the resulting green light to a suitable level within the desired range.

Figure 8:
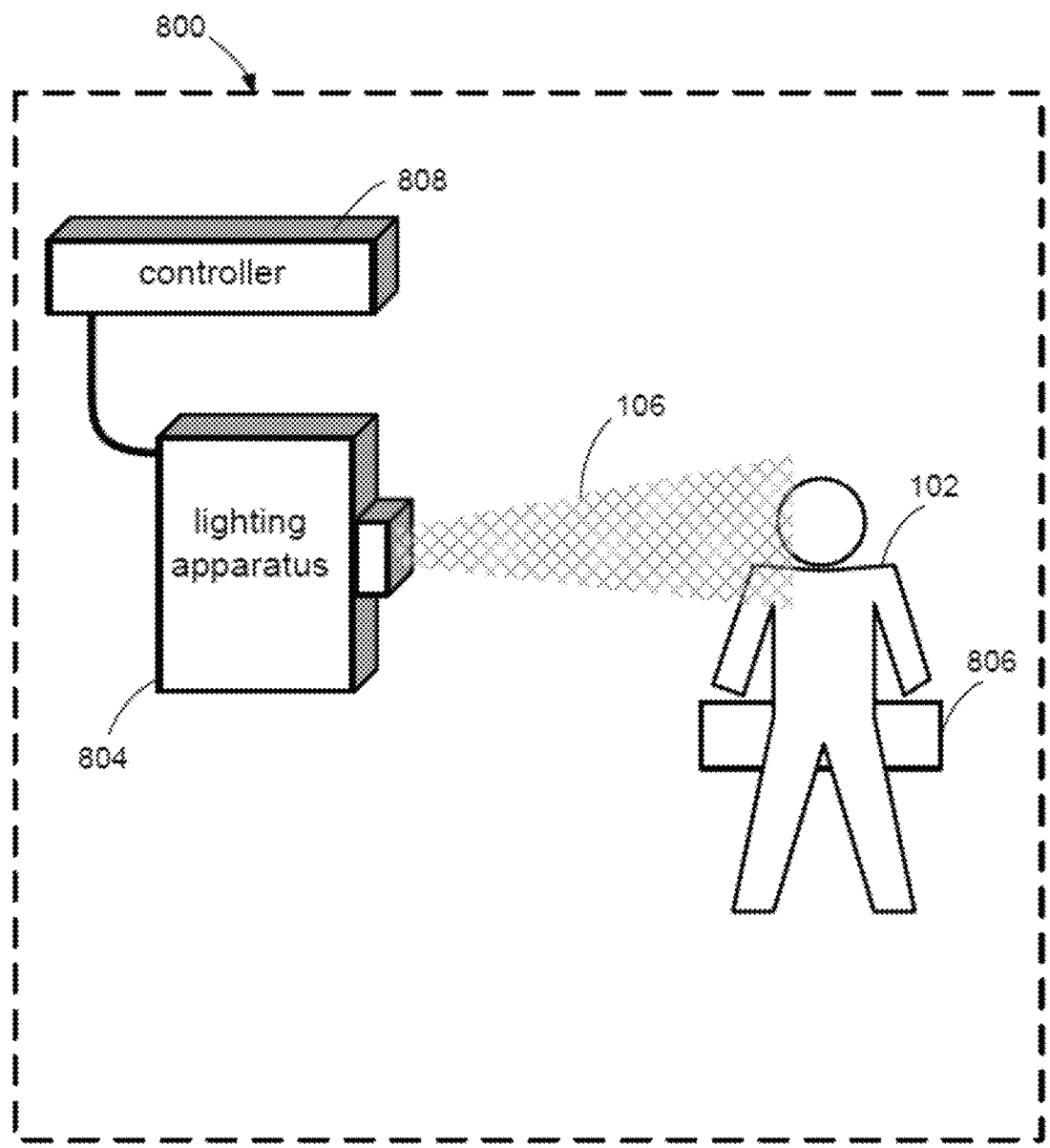
FIG. 8 depicts an environment in which a patient suffering from a migraine may be treated.

According to some embodiments, patients suffering from migraine may be treated in a clinical setting, as depicted in FIG. 8. In some embodiments, a person may be exposed to the narrow-band green illumination in a specially designed environment. For example, a lighting apparatus 804 capable of producing illumination having a characteristic wavelength at 530 nm and limited to a narrow bandwidth in the green portion of the visible spectrum may be positioned in an area 800 (e.g., a room in a medical facility) in which outside lights and sounds can be blocked or suppressed. FIG. 8 schematically depicts an example of such area 800 comprising a lighting apparatus 804 and controller 808, which, in some embodiments, may be similar to lighting apparatus 104 and controller 108 (FIG. 1), respectively. In other embodiments, the lighting apparatus 804 and controller 808 may be included in a photic stimulator, such as, for example, ColorDome® manufactured by Diagnosys LLC (Lowell, Mass.). It should be appreciated that area 800 may comprise any other components, which are not shown for the sake of simplicity.

Area 800 may be enclosed and may provide a comfortable environment for a person. As shown in FIG. 8, area 800 may include a seat 806 where person 102 may be seated in front of lighting apparatus 804, which can produce illumination 106 having a characteristic wavelength of 530 nm. While person 102 is being exposed to the light, the room may be darkened, either partially or completely, to eliminate other wavelengths and thus increase the efficacy of the exposure. A person suffering from severe migraines may receive multiple sessions of exposure to the illumination in such a controlled environment.

When a patient is located in a controlled area 800, such as in a physician's office or a specially designed area, a lighting apparatus 804 may be activated upon an action by a physician or in response to other trigger. The patient may be instructed to keep his/her eyes open to view the light. In embodiments where a migraine sufferer is using a portable device (e.g., in a home, office or other environment), exposure to the light using the described techniques may be initiated by the user of such device. For example, when a light source is incorporated into a desk lamp or other device typically located in the vicinity of the user, the user may simply turn on a switch, press a button or otherwise instruct the light source to emit light of a desired wavelength.

In some embodiments, a patient may be exposed to narrow-band illumination having a characteristic wavelength of 530 nm using the processes described above during a single session or in multiple sessions. A number and duration of sessions and operating parameters of a lighting apparatus may be selected depending on the severity and frequency of migraine and other factors. A duration of the session may be defined in advance. The duration of a session may be controlled by an operator of the light emitting device, such as a physician or other medical professional, or in other ways. The operating parameters of the lighting apparatus 804 may be selected so that the patient is exposed to the narrow-band illumination having a luminance value in a range from approximately 1 $cd/m^2$ to approximately 5 $cd/m^2$, according to some embodiments. In some cases, the range may be from approximately 1 $cd/m^2$ to approximately 70 $cd/m^2$. It should be appreciated, however, that embodiments are not limited to only these light intensities. In some embodiments, the characteristic wavelength of the green illumination may be slightly lower or higher than 530 nm. In some cases, the characteristic wavelength may be as short as 510 nm. In other cases, the characteristic wavelength may be as long as 550 nm. In some embodiments, a bandwidth of the illumination may be as large as 30 nm, or even as large as 40 nm in other cases.

EXAMPLES

In initial trials, the inventor conducted studies involving 35 subjects experiencing photophobia induced by migraines. A photic stimulator, ColorDome® manufactured by Diagnosys LLC (Lowell, Mass.), was used to produce light at different colors, and the subjects were exposed to a selected color of light. The sensitivity of the subjects to different colors of light was tested both interictally (when migraine-free) and ictally (during migraine). Focusing on the ability of light to alter pain perception, it was discovered that an exposure to different colors of light during migraine affect the pain differently—exacerbate the pain, trigger or induce throbbing, and expand the headache from one side to the other and/or from periorbital to occipital areas.

Further, the inventor discovered that exposure to light of some colors within the visible portion of the electromagnetic spectrum may trigger or worsen nausea, dizziness, sweating, tearing, salivation, crying, panic, anxiety, tingling, itching and other symptoms. For example, exposure to light perceived as white, blue, yellow, amber and red lights may worsen pain and the throbbing as well as cause negative emotions and autonomic response, such as tearing, lump in the throat, and anxiety.

However, it was discovered that exposure to green light having a characteristic wavelength of 530 nm and narrow bandwidth did not exacerbate photophobic symptoms. In contrast and quite surprisingly, many subjects exhibited reduced photophobia and a mitigation of migraine pain. Some subjects reported experiencing increased calmness when subjected to the narrow-band illumination. Increased beneficial effects were observed when the luminance was in a range from 1 $cd/m^2$ and 5 $cd/m^2$ at a distance of one foot.

The results from the initial trials were used to determine conditions which may allow a person to continue performing normal tasks while experiencing photophobia. Thus, luminance of a lighting apparatus was calculated that would provide a luminance value appropriate for a subject at a "working distance" from the apparatus. A "working distance" is a distance from the lighting apparatus at which the user's eyes are located or a distance from the lighting apparatus at which an object illuminated by the lighting apparatus and handled by the user is located (e.g., a desk, a book). The working distance may be specified for a lighting apparatus, so that a user knows how to use the lighting apparatus. As an example, if a person is working at his or her desk and the lighting apparatus is a desk lamp or a similar lamp, the working distance may be about 1.5 feet. The specification may indicate that the lighting apparatus provides up to 5 cd/m² at a working distance of 1.5 feet. If the lighting apparatus is a ceiling light, the working distance may be approximately 4-6 feet. Accordingly, the luminance at a lighting apparatus for different working distances may be as follows:

TABLE 2

Source luminance based on a distance between a subject and a light source.

| Working distance (feet) | Luminance at lighting apparatus (cd/m²) | |
|---|---|---|
| | 1 | 5 |
| 1.5 | 50 | 250 |
| 2 | 100 | 500 |
| 4 | 400 | 2000 |
| 6 | 700 | 3500 |

Figure 9:
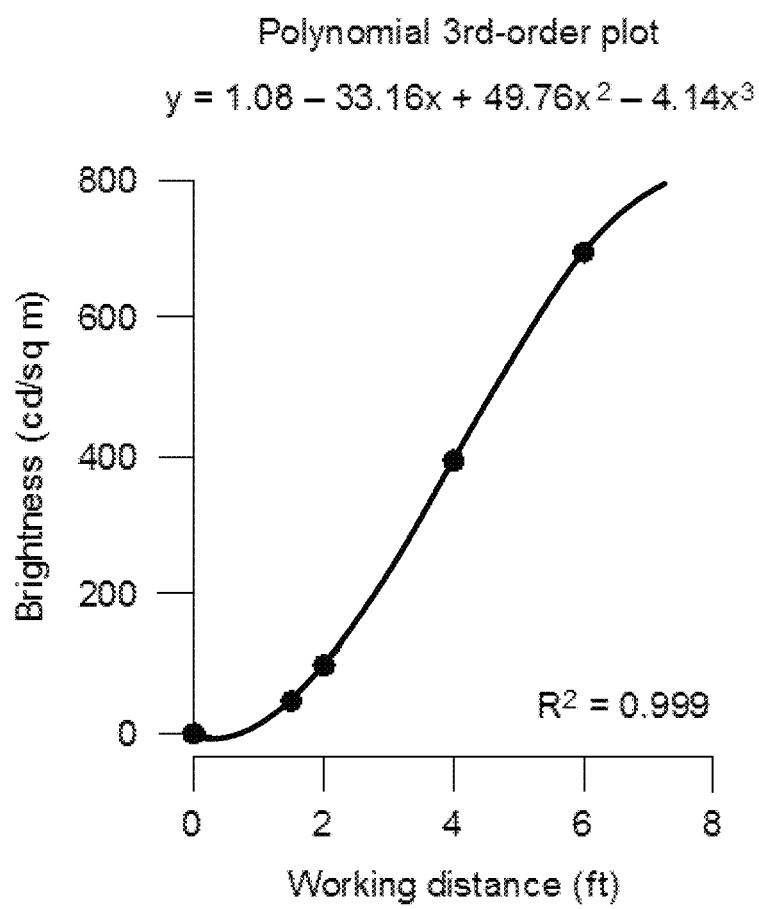
FIG. 9 plots a dependency of luminance from a source on a distance between a person and a light source, according to an embodiment.

A graph showing dependency of luminance on a distance between a subject and a lighting apparatus is illustrated in FIG. 9. FIG. 9 is calculated for a luminance value at the subject of approximately 1 cd/m².

In subsequent trials, the inventor studied 124 subjects' responses to different colors and luminances of light under different conditions. Of the 124 subjects, 80 were migraine patients, 33 were healthy subjects, 7 were diagnosed with migraine and ocular diseases that render them blind, and 4 were diagnosed with photophobia due to ocular diseases but not due to migraine.

For the 80 migraine patients, 31 were enrolled in a 'pilot' phase of the study and 49 in a second 'complete' phase of the study. Of the 31 patients enrolled in the 'pilot' phase, 16 completed visit 1 (when pain-free) and visit 2 (during migraine), 9 completed visit 2 only (during migraine), and 6 completed visit 1 only (when pain-free). In these visits, only the subjects' sensitivity to different colors of light was documented. Electroretinography (ERG) and visual evoked potential (VEP) were not documented.

Of the 49 migraine patients enrolled in the 'complete' phase of the study, 14 completed visit 1 and 2, 46 completed visit 1 (when pain-free), and 3 completed visit 2 only (during migraine). By combining the 2 phases of this study, a database was created consisting of successful documentation of light sensitivity testing in 42 migraine patients during migraine, 59 migraine patients in the absence of migraine, and 43 ERG testing in migraine patients. VEP was also recorded in these 43 patients.

Fifteen of the 33 healthy subjects completed all three parts of the study. Of the seven blind subjects, three completed all parts of the study (visit 1 while pain-free, visit 2 during migraine, light sensitivity part, ERG part, and VEP part).

Figure 10A:
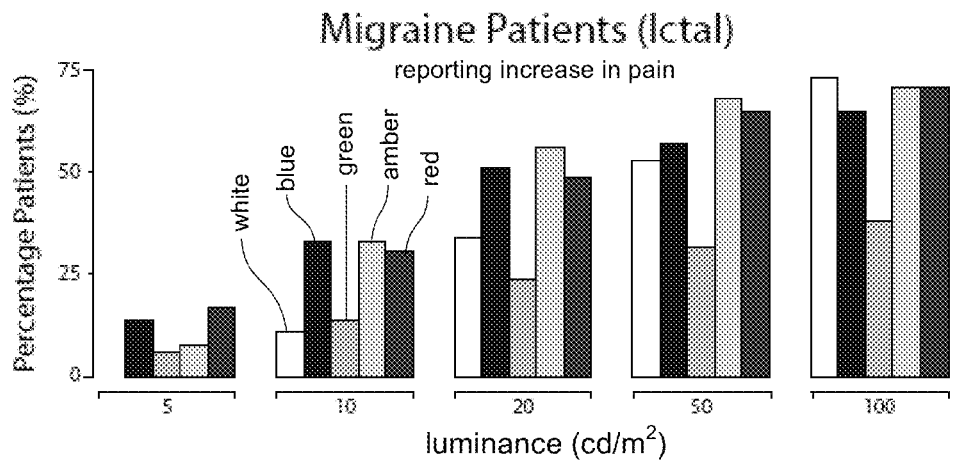
FIG. 10A plots percentages of migraine patients reporting increased pain intensity when exposed to different colors of light at different luminance values.
Figure 10B:
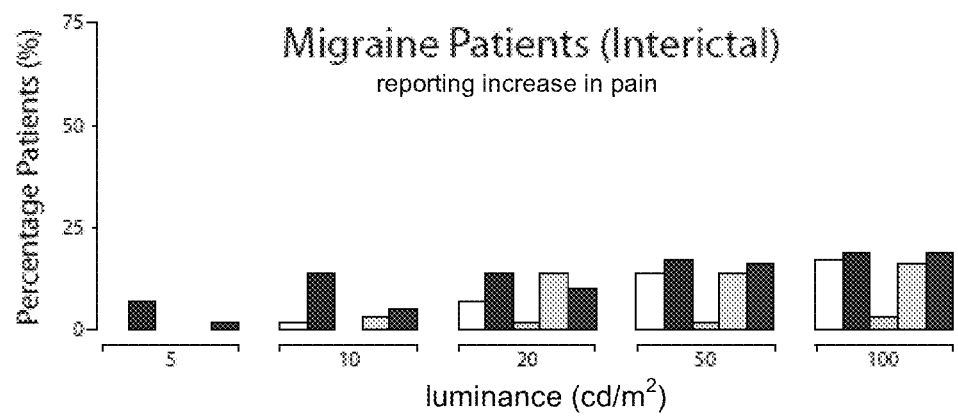
FIG. 10B plots percentages of migraine patients reporting onset of pain when exposed to different colors of light at different luminance values.
Figure 10C:
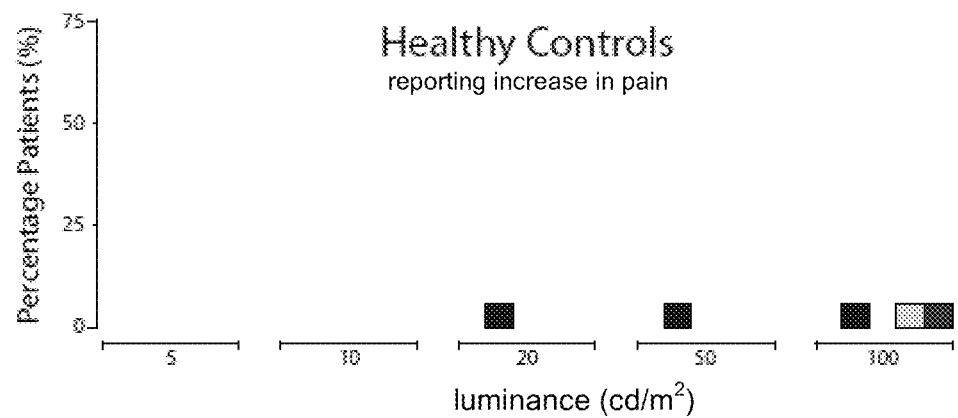
FIG. 10C plots percentages of healthy individuals reporting onset of pain when exposed to different colors of light at different luminance values.

Results from these trials are plotted in FIG. 10A through FIG. 12B. More than 70% percent of the patients reported increased pain intensity when exposed to different colors of light, as indicated in FIG. 10A. In contrast to the notion that exposure to blue light is most likely to increase pain intensity during migraine, it was found that headache pain intensity increased similarly when patients are exposed to white, blue, amber and red light. At low luminance values, only 10-20% of the patients report exacerbation of headache pain whereas at high luminance values, 65-73% of the patients experience intensification of headache. These findings suggest that there are ways to allow patients to continue with their daily activities in the light—in spite of being photophobic.

It was also found that when migraine patients are pain-free (interictal), exposure to white, blue, amber or red light can trigger headache-like pain or ocular pain in 10-20% of them. This can be seen from FIG. 10B, which plots interictal patients reporting onset of pain following exposure to different colors of light.

Figure 11:
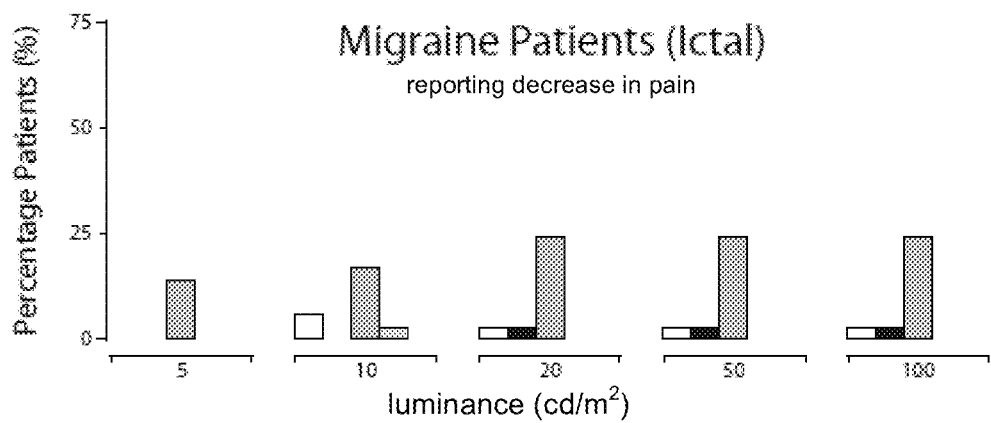
FIG. 11 plots percentages of migraine patients reporting decreased pain intensity when exposed to different colors of light at different luminance values.

A significant finding is that exposure to narrow-band green light is associated with a significantly lower incidence of headache intensification (FIG. 10A). Some subjects reported a decrease in the intensity of the headache when exposed to green light, which is plotted in FIG. 11. FIG. 11 plots percentages of patients reporting a decrease in migraine pain following exposure to different colors of light at different luminance values.

Figure 12A:
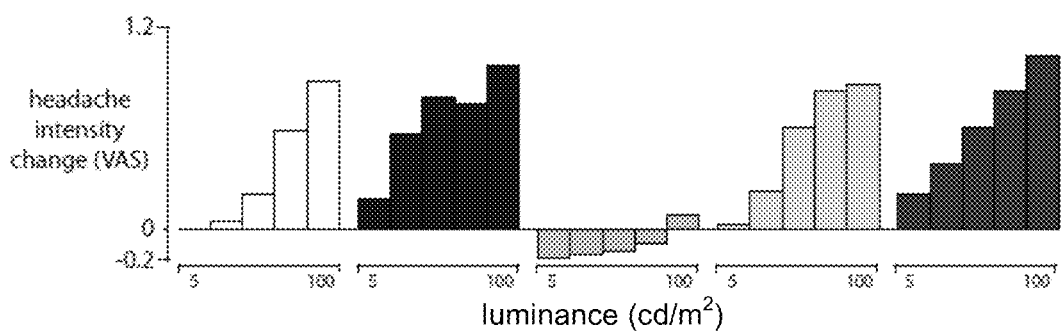
FIG. 12A plots mean changes in headache intensity (according to a visual analog scale) reported by patients during migraine when exposed to different colors of light at different luminance values.

The findings that exposure to white, blue, amber and red light is equally painful was further supported by data showing by how much the pain intensified. The intensification of pain (or reduction for green illumination) is plotted in FIG. 12A. When quantified according to a 0-10 visual analog scale (VAS), the intensity of the headache increased by about 10% when patients were exposed to all colors but green. When exposed to green the headache intensity decreased slightly, by about 2%. The values in FIG. 12A summarize all patients, those reporting intensification of headache by light and those who do not report such experience.

Figure 12B:
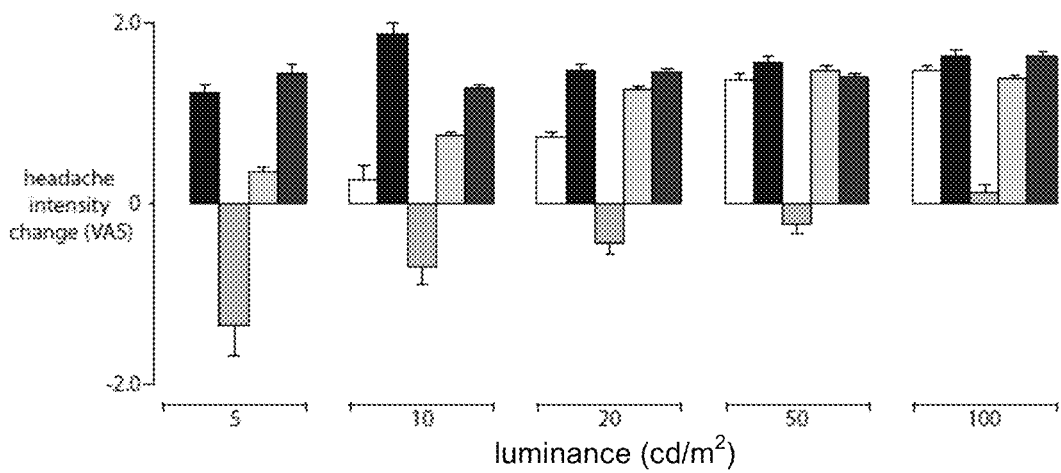
FIG. 12B plots mean changes in headache intensity (according to a VAS) reported by patients exhibiting changes during migraine when exposed to different colors of light at different luminance values.

When these data were computed based on cases in which headache was intensified but not cases in which it wasn't (i.e., determining by how much the pain intensifies when it does), the results indicate that when white, blue, amber, and red light intensify a headache, the increase in pain is about 15%, as shown in FIG. 12B. Also, the magnitude of pain increase did not depend appreciably on the luminance of the light.

In contrast, when green light decreased the headache intensity, it decreased it by nearly 15% at low luminance values (from 1 cd/m² to about 5 cd/m²). When the intensity of the green light was maximal (100 cd/m²) the headache intensity increased slightly. Collectively, these data suggest that exposure to low or mid-luminance green light (e.g., less than about 70 cd/m²) may be beneficial for patients and allow them to resume visual tasks while recovering from migraine.

Having thus described several aspects of at least one embodiment, it is to be appreciated that various alterations, modifications, and improvements will readily occur to those skilled in the art. Such alterations, modifications, and improvements are intended to be part of this disclosure, and are intended to be within the spirit and scope of the invention. Further, though advantages of some embodiments are indicated, it should be appreciated that not every embodiment will include every described advantage. Some embodiments may not implement any features described as advantageous herein and in some instances. Accordingly, the foregoing description and drawings are by way of example only.

What is claimed is:

1. A method comprising:
providing an enclosed environment for a subject;
blocking substantially all visible radiation from the enclosed environment; and
lighting the enclosed environment with radiation at a characteristic wavelength only in a wavelength range between 510 nm and 550 nm with a bandwidth no larger than 20 nm full-width-half-maximum.

2. The method of claim 1, wherein the luminance produced to light the enclosed environment is between approximately 1 cd/m2 and approximately 70 cd/m2 at a location of the subject.

3. The method of claim 2, wherein the luminance produced is between approximately 1 cd/m2 and approximately 30 cd/m2 at the location of the subject.

4. The method of claim 2, wherein the luminance produced is between approximately 1 cd/m2 and approximately 10 cd/m2 at the location of the subject.

5. The method of claim 2, wherein the luminance produced is between approximately 1 cd/m2 and approximately 5 cd/m2 at the location of the subject.

6. The method of claim 1, wherein the characteristic wavelength is 530 nm.

7. The method of claim 1, wherein the characteristic wavelength is 520 nm.

8. A method comprising:
providing an enclosed environment;
eliminating outside sources of red and blue light from the enclosed environment; and
lighting the enclosed environment with radiation at a characteristic wavelength only in a wavelength range between 510 nm and 550 nm with a bandwidth no larger than 20 nm full-width-half-maximum.

9. The method of claim 8, further comprising producing a luminance between approximately 1 cd/m2 and approximately 70 cd/m2 at a location of a subject.

10. The method of claim 9, wherein the luminance produced is between approximately 1 cd/m2 and approximately 30 cd/m2 at the location of a subject.

11. The method of claim 9, wherein the luminance produced is between approximately 1 cd/m2 and approximately 10 cd/m2 at the location of a subject.

12. The method of claim 9, wherein the luminance produced is between approximately 1 cd/m2 and approximately 5 cd/m2 at the location of a subject.

13. The method of claim 8, wherein the characteristic wavelength is 530 nm.

14. The method of claim 8, wherein the characteristic wavelength is 520 nm.

15. The method of claim 8 further comprising eliminating all outside lights from the enclosed environment.

16. The method of claim 8, wherein the eliminating is of visible radiation from natural light and the lighting is provided by the natural light.

17. A method comprising:
providing an enclosed environment;
blocking red and blue radiation from the enclosed environment;
lighting the enclosed environment with radiation at a characteristic wavelength only in a wavelength range between 510 nm and 550 nm with a bandwidth no larger than 20 nm full-width-half-maximum; and
producing a luminance between approximately 1 cd/m2 and approximately 70 cd/m2 at a location of the subject.

18. The method of claim 17, wherein the luminance produced is between approximately 1 cd/m2 and approximately 30 cd/m2 at the location of the subject.

19. The method of claim 17, wherein the luminance produced is between approximately 1 cd/m2 and approximately 10 cd/m2 at the location of the subject.

20. The method of claim 17, wherein the luminance produced is between approximately 1 cd/m2 and approximately 5 cd/m2 at the location of the subject.

21. The method of claim 17, wherein the characteristic wavelength is 530 nm.

22. The method of claim 17, wherein the characteristic wavelength is 520 nm.

23. The method of claim 17 wherein all visible radiation is blocked from the enclosed environment.

* * * * *